United States Patent [19]
Scarborough et al.

[11] Patent Number: 5,846,484
[45] Date of Patent: Dec. 8, 1998

[54] PRESSURE FLOW SYSTEM AND METHOD FOR TREATING A FLUID PERMEABLE WORKPIECE SUCH AS A BONE

[75] Inventors: Nelson L. Scarborough, Wayside; John W. Morris, Beachwood; James L. Russell, Little Silver; Michael Dowd, Eastampton, all of N.J.

[73] Assignee: Osteotech, Inc., Eatontown, N.J.

[21] Appl. No.: 821,603

[22] Filed: Mar. 20, 1997

[51] Int. Cl.⁶ .................................................. A61M 31/00
[52] U.S. Cl. ............................ 422/28; 128/898; 422/33; 422/292; 422/295; 422/296; 422/297; 604/49; 623/16
[58] Field of Search .................................. 422/27, 28, 33, 422/292, 295, 296, 297; 604/28, 49; 623/16; 128/898

[56] References Cited

U.S. PATENT DOCUMENTS

| | | |
|---|---|---|
| 2,686,138 | 8/1954 | Klein . |
| 2,943,632 | 7/1960 | Bush . |
| 3,038,732 | 6/1962 | Scott et al. . |
| 3,056,698 | 10/1962 | Kleesattel et al. . |
| 3,665,547 | 5/1972 | Boylan . |
| 4,993,722 | 2/1991 | Gundy . |
| 5,037,437 | 8/1991 | Matsen, III . |
| 5,263,503 | 11/1993 | St. Jean . |
| 5,275,954 | 1/1994 | Wolfinbarger et al. ................... 436/74 |
| 5,322,081 | 6/1994 | Isaac . |
| 5,333,626 | 8/1994 | Morse et al. . |
| 5,377,216 | 12/1994 | Nilsen et al. . |
| 5,511,568 | 4/1996 | Bowman et al. . |
| 5,513,662 | 5/1996 | Morse et al. . |
| 5,542,442 | 8/1996 | Gorman, Sr. . |
| 5,556,379 | 9/1996 | Wolfinbarger . |

Primary Examiner—Krisanne Thornton
Attorney, Agent, or Firm—Dilworth & Barrese

[57] ABSTRACT

A pressure flow system and method for its use are provided for contacting the interior of a fluid permeable, e.g., porous, workpiece. The system includes a fluid pressure chamber having an inlet port and an opening formed in one of the chamber walls. An adjustable seal capable of providing a fluid-tight seal about the exterior of a workpiece having a non-uniform surface is positioned within the opening. Fluid under pressure is supplied to the pressure chamber to force fluid to flow through the internal matrix of the workpiece. In a preferred embodiment, the workpiece is a bone or a section thereof, and the fluid is forced to flow from the endosteal portion of bone to the periosteal portion of bone through the vasculature and porous structure of the bone to remove blood, bone marrow and/or other non-bone constituent(s) from the bone. Alternatively, the fluid can be chosen to decontaminate and/or demineralize the bone, to stain the bone to improve visualization of the bone microvasculature or to impregnate with pharmacological agents (antibiotics, bone growth factors, etc.) so that bone can act as a delivery system.

29 Claims, 8 Drawing Sheets

PRESSURE FLOW SYSTEM AND METHOD FOR TREATING A FLUID PERMEABLE WORKPIECE SUCH AS A BONE

BACKGROUND

1. Technical Field

This invention relates to an apparatus and method for treating, e.g., cleaning, the interior of a fluid permeable workpiece by establishing a flow of fluid using pressure differentials. More specifically, the present invention provides a pressure flow system for accessing the internal porous matrix of bone that is intended for implantation with one or more treatment fluids to variously clean, defat, sterilize, virally inactivate, disinfect, and/or demineralize the bone, to facilitate the visualization of its structure or to impregnate the bone with one or more pharmacological agents (antibiotics, bone growth factors, etc.) so the bone can act as a drug delivery system.

2. Background of Related Art

The preparation of bone tissue for subsequent implantation involves one or more aseptic cleaning procedures that are intended to minimize the risk of transferring potentially harmful disease organisms to tissue recipients and to reduce transplant-related antigenicity. Known bone cleaning procedures are not always completely and/or consistently effective. Accordingly, there is a risk that in employing any of the known bone cleaning procedures, harmful microorganisms and/or antigenic material may continue to reside in bone.

U.S. Pat. No. 5,333,626 discloses a method for preparing bone for transplantation in which the bone is first contacted with a decontaminating agent and subsequently contacted with detergent under high pressure washing conditions at elevated temperatures. U.S. Pat. Nos. 5,513,662 and 5,556,379 disclose the application of a less than ambient pressure, i.e., vacuum, to facilitate displacement of removable material from the internal matrix of bone as a method of preparing the bone for transplantation. Although the above-described methods have realized some success, difficulties have been encountered in uniformly penetrating deep into the bone matrix where infectious agents and/or immunogenic macro-molecules may be present.

Accordingly, a need exists for an improved apparatus and process for cleaning and decontaminating a bone which minimizes exposure of a transplant recipient to potentially harmful diseases and transplant related antigenicity. The disclosed system further provides a method to treat bone with agents that can result in improved performance characteristics, to act as a means to deliver one or more bioactive agents to a body in which the bone is implanted, to allow for staining of bone for diagnostic or research purposes or to study the fluid flow characteristics of bone and its microvasculature.

SUMMARY

In accordance with the present disclosure, a pressure flow system and method are provided for treating a fluid permeable workpiece. The system includes at least one fluid subsystem for supplying a treatment fluid to a fluid pressure chamber. The fluid pressure chamber is constructed having an inlet port and an opening formed in one of the chamber walls. An adjustable seal capable of providing a fluid-tight seal about the exterior of a fluid permeable workpiece having a non-uniform exterior surface is positioned within the opening. Treatment fluid under pressure is supplied to the pressure chamber from the fluid subsystem to force the fluid to flow through the internal matrix of the workpiece so as to alter, modify or otherwise affect some aspect of the workpiece. In a preferred embodiment, the fluid permeable workpiece is a bone or a section thereof and the fluid is a cleaning or disinfecting fluid which is forced to flow through the vasculature and porous structure of the bone to effect the removal of blood, bone marrow and/or other non-bone constituent(s) from the bone, and/or sterilize and virally inactivate the bone. Alternately, the pressure flow system can be employed to demineralize bone, to stain the microvasculature of bone to improve its visualization or to introduce bioactive agents.

The expression "fluid permeable workpiece" as used herein shall be understood to include any article, device, material, or the like, which permits the passage of a fluid under pressure therethrough. The term "fluid" includes all liquid and gaseous treatment substances, and their mixtures, that are flowable under the conditions of operation of the pressure flow system.

BRIEF DESCRIPTION OF THE DRAWINGS

Various preferred embodiments are described herein with reference to the drawings, wherein.

DETAILED DESCRIPTION OF PREFERRED EMBODIMENTS

Preferred embodiments of the presently disclosed pressure flow system will now be described in detail with reference to the drawings in which like reference numerals designate identical or corresponding elements in each of the several views.

Figure 1:
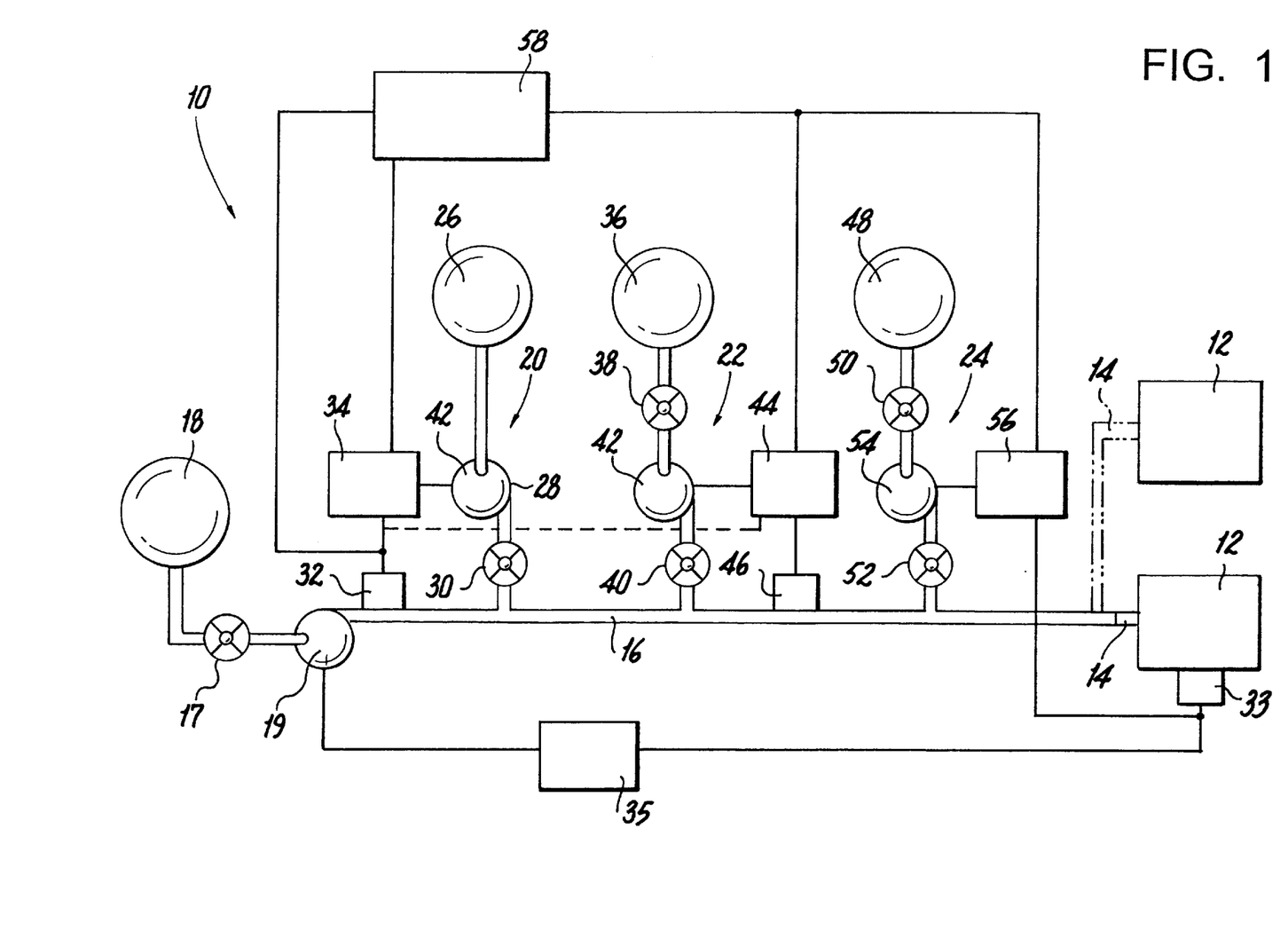
FIG. 1 is a schematic view of one embodiment of the pressure flow system.

FIG. 1 illustrates one embodiment of the presently disclosed pressure flow system shown generally as 10. Briefly, pressure flow system 10 includes at least one pressure chamber 12 having an inlet 14 communicating with one end of a fluid supply manifold 16. The other end of manifold 16 communicates with a water supply source 18 and a plurality of treatment fluid subsystems 20, 22, and 24. Subsystems 20, 22 and 24 supply treatment fluids to pressure chamber 12 to treat a fluid permeable workpiece mounted partially therein. Although system 10 is disclosed as having three fluid subsystems, more or fewer such subsystems can be provided to suit the particular process being used. Water from water supply source 18 is supplied through water valve 17 to manifold 16 by pump 19. Flow controller 35 communicates with pressure transducer 33 mounted on pressure chamber 12 to control the speed of pump 19 to maintain a constant pressure in chamber 12. Flow transducer 32 is positioned on manifold 16 between pump 19 and subsystem 20 to measure the water flow rate through manifold 16 upstream of subsystems 20, 22 and 24. Subsystems 20, 22 and 24 will be described in further detail below.

Figure 2:
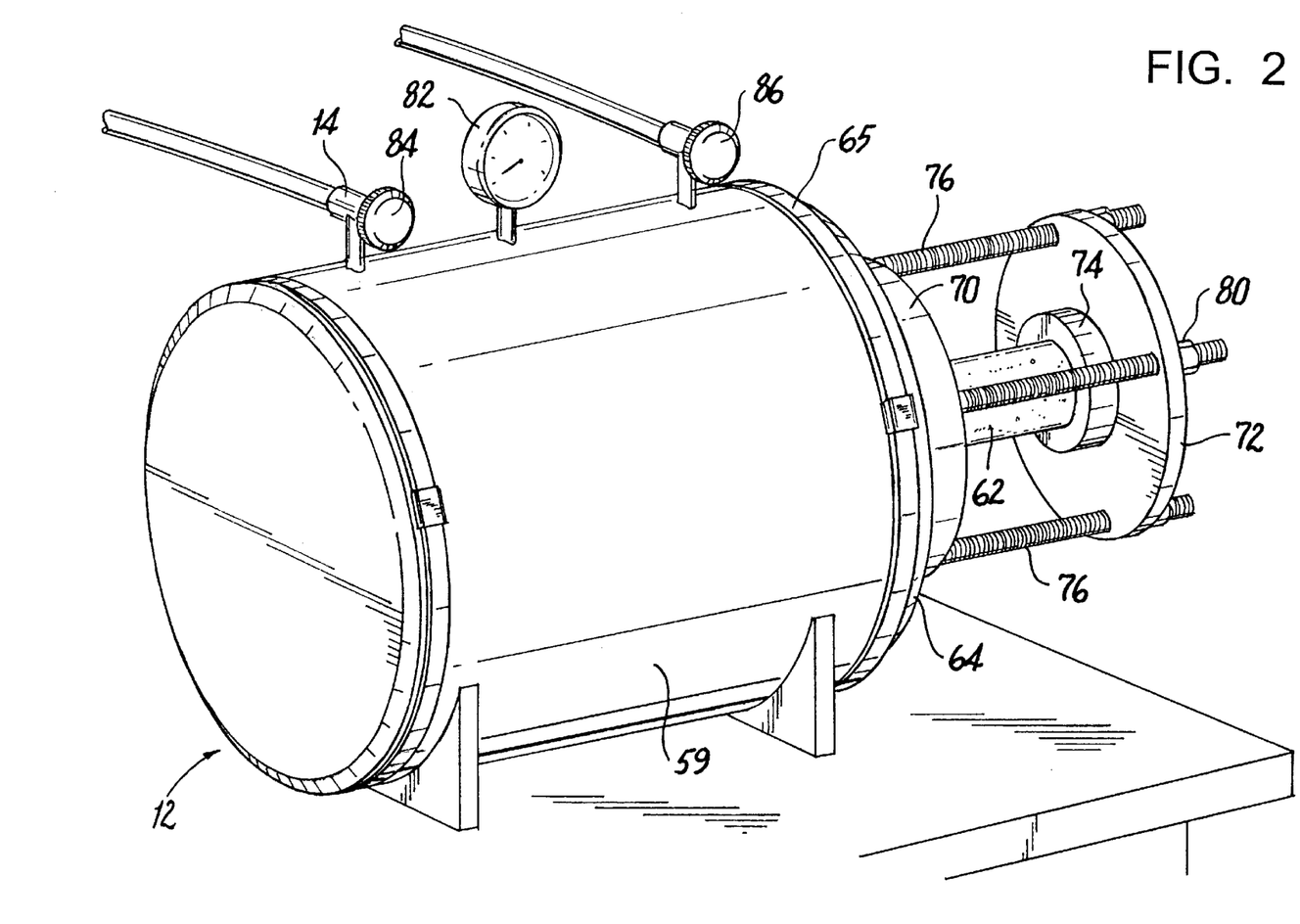
FIG. 2 is a side perspective view of the cleaning chamber of the pressure flow system shown in FIG. 1.
Figures 3, 4:
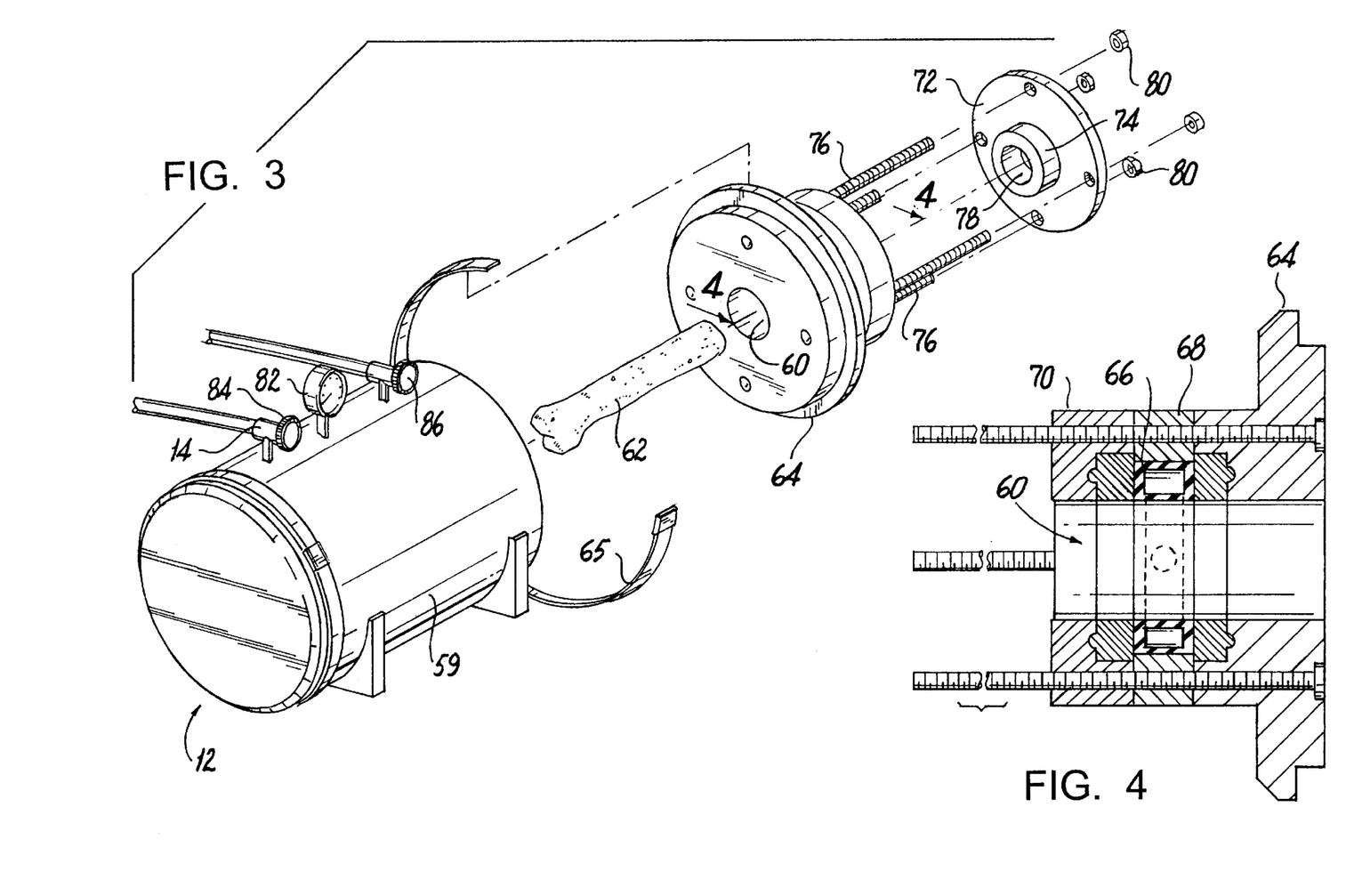
FIG. 3 is a side perspective view with parts separated of the cleaning chamber of the pressure flow system shown in FIG. 2.
FIG. 4 is a cross-sectional view taken along line 4—4 of FIG. 3.

Referring now to FIGS. 2–4, pressure chamber 12 includes a chamber body 59 having an opening 60 formed in one of the chamber walls and dimensioned to receive a fluid permeable workpiece 62. In the embodiment shown, the workpiece is a bone or section of bone, the porous internal structure of which permits the flow of pressurized fluid therethrough. Although illustrated as having a cylindrical shape, chamber 12 can be rectangular, box-like, or any other shape capable of supporting bone 62 and receiving a pressurized fluid. Chamber 12 can also have multiple openings such that several workpieces can be accommodated in the same chamber. Preferably, opening 60 is formed in removable end cap 64 which is secured to one end of chamber 12 using easily removable fasteners known in the art. End plate 64 is removable to gain access to the interior of chamber 12 for positioning bone section 62 therein or for cleaning the interior of chamber 12. Band 65 can be used to secure end plate 64 to body 59. An adjustable seal 66 capable of providing a fluid-tight seal about the exterior of the bone (which has a somewhat irregular cross-section) surrounds opening 60. Seal 66 can be any type of seal satisfying the foregoing requirements and is advantageously a pneumatically or hydraulically adjustable seal which can be selectively pressurized to sealingly engage the exterior surface of the bone no matter how irregular its cross-section. Seal 66 is supported within collar 68 positioned between end plate 64 and spacer member 70.

A retainer plate 72 having a blocking collar 74 is supported on rods 76 in front of opening 60. Blocking collar 74 is preferably aligned with opening 60 to engage one end of workpiece 62 to prevent the workpiece from shifting within opening 60 as a result of the pressure differential across seal 66. A sealing member 78 which can be an elastomeric pad capable of deforming around the end of workpiece 62 can be fitted in blocking collar 28 to provide a fluid tight seal about one end of workpiece 62. Retaining nuts 80 are movably secured to rods 76 to permit adjustment of retainer plate 72 with respect to end plate 64. Rods 76 can also be used to secure end plate 64, collar 68 and spacer member 70 to chamber 12, although other fastening devices can also be used for this purpose. Chamber 12 is provided with a pressure gauge 82, a fluid inlet valve 84, an air vent valve 86 and a drain (not shown). Valves 84 and 86 can be electrically actuated valves controllable from master controller 58 (See FIG. 1).

Figure 5:
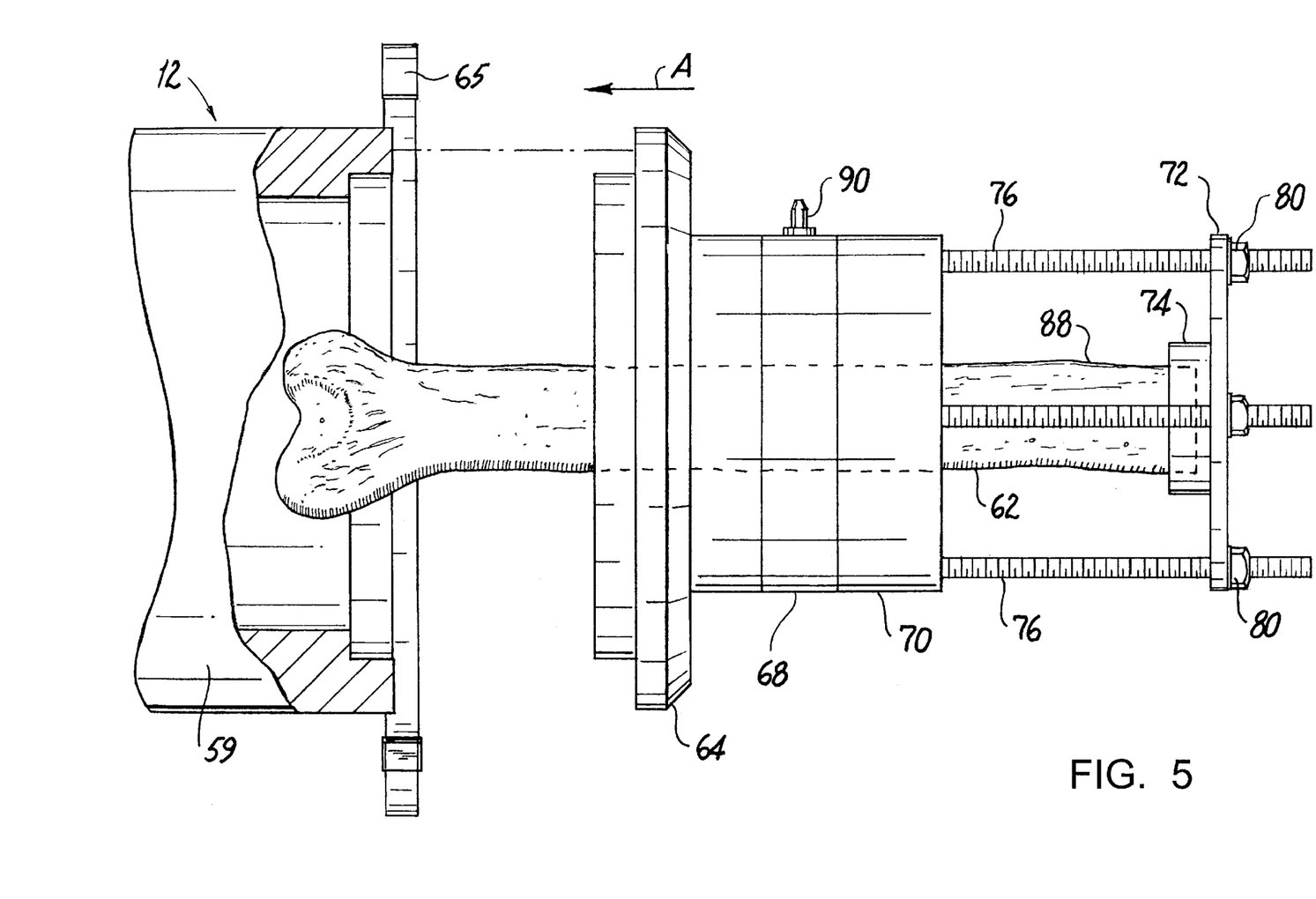
FIG. 5 is a side partial cross-sectional view of one end of the cleaning chamber with the end plate removed and a fluid permeable workpiece, specifically, a section of bone, positioned within the chamber opening.
Figure 6:
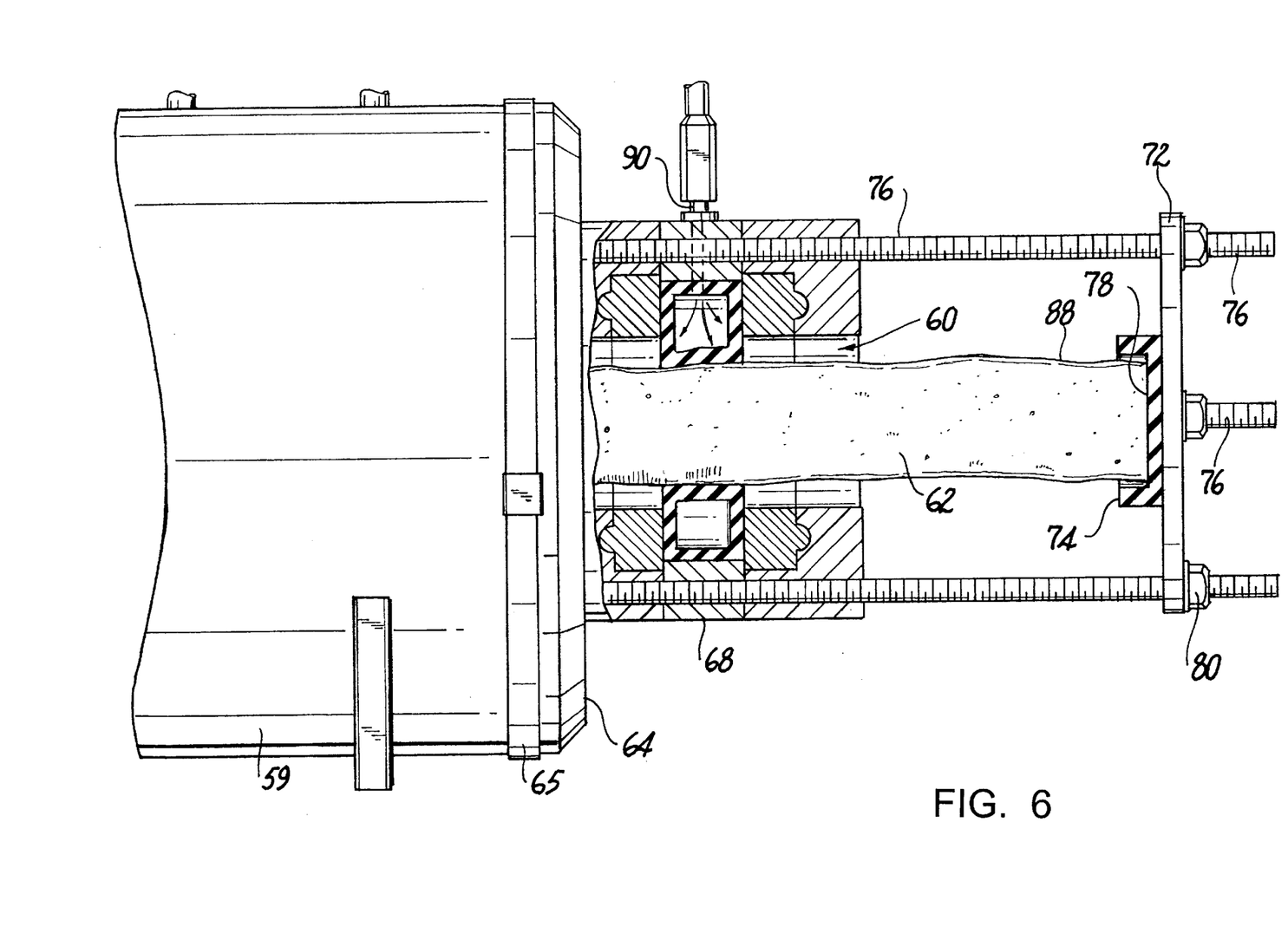
FIG. 6 is a side partial cross-sectional view of one end of the cleaning chamber with a section of bone secured therein.
Figure 7:
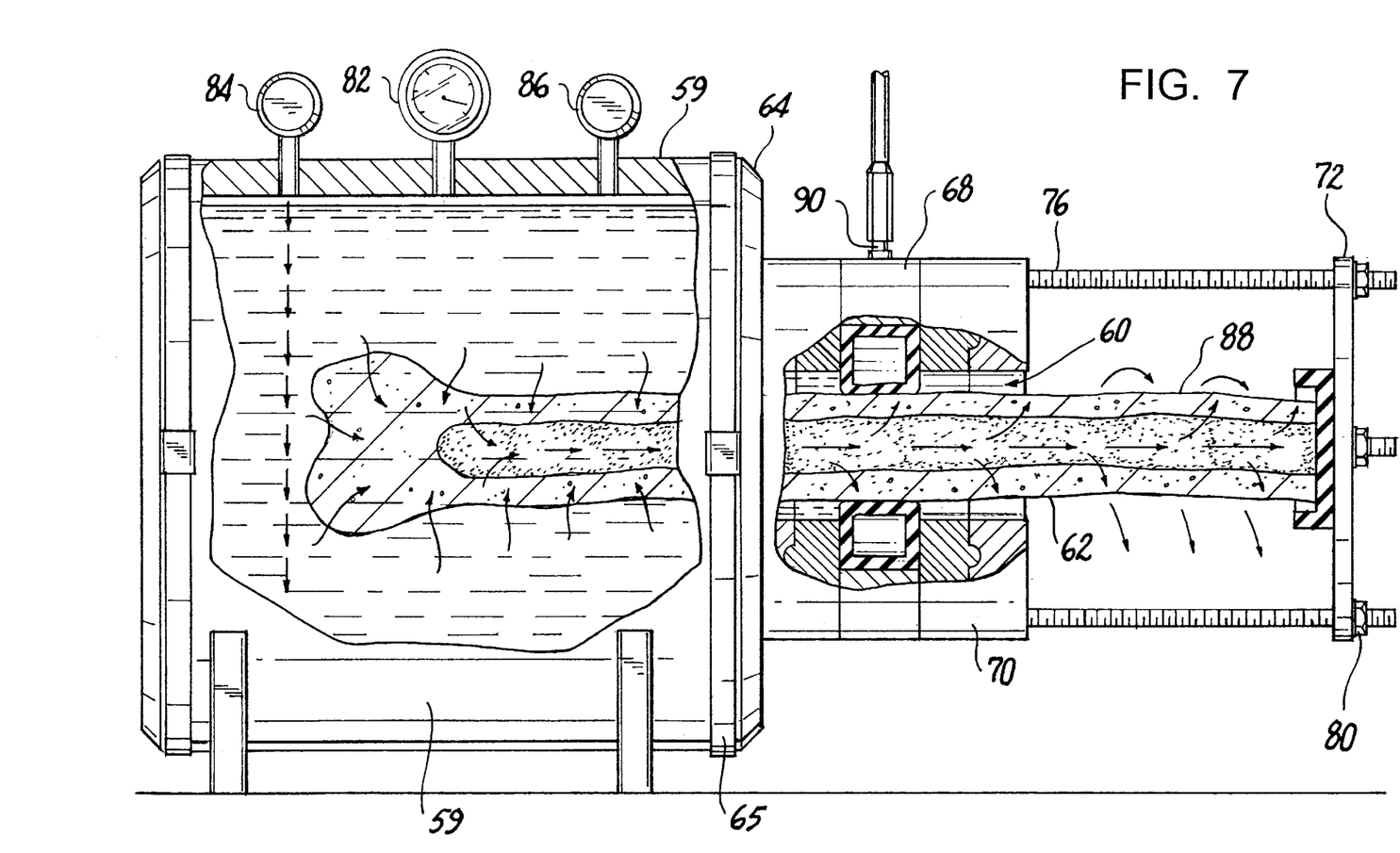
FIG. 7 is a side partial cross-sectional view of the cleaning chamber with a section of bone secured therein and pressurized fluid being forced through the workpiece.

Referring now to FIGS. 5–7, bone section 62 is secured within chamber 12 by removing end cap 64 from chamber body 59 and sliding first end 88 of bone section 62 through opening 60 in end cap 64 towards retainer plate 72. First end 88 is positioned within blocking collar 74 on retainer plate 72. Preferably, the position of retainer plate 72 is adjusted on rods 76 to position the greater portion of the length of bone section 62 outside opening 60 with only a small portion of the bone being positioned within chamber 12. After retainer plate 72 is properly adjusted, end cap 64 can be secured to chamber body 59 by moving the end cap in the direction indicated by arrow A in FIG. 5.

Referring to FIG. 6, collar 68 includes a valved port 90 for pressurizing adjustable seal 66. After bone section 62 is properly positioned in pressure chamber 12 and end cap 64 is secured to chamber body 59, fluid pressure is supplied to adjustable seal 66 to provide a fluid-tight seal within opening 60 about the bone. As illustrated in FIG. 7, after bone section 62 is properly sealed, fluid at a predetermined pressure is supplied through inlet 14 to chamber 12. Because of the pressure differential across adjustable seal 66, pressurized fluid within chamber 12 is forced from chamber 12 through the porous internal matrix of the bone.

Referring again to FIG. 1, pressure flow system 10 is particularly suited for treating bones, including cadaveric long bones, ilium, ribs, etc., intended for surgical implantation. In a preferred embodiment of pressure flow system 10 for treating bone, a fluid subsystem, e.g., fluid subsystem 20, includes a surface active agent of the anionic, cationic, amphoteric and/or non-ionic variety. Preferably, the surface active agent is a non-ionic octylphenoxy polyethoxy ethanol 26 suitable for removing protein and lipids from bone, such as Triton X-100™ (Rohm and Haas Co.), although other surface active agents can also be used. Fluid pump 28, which is preferably a peristaltic pump although other kinds of pumps can be used, supplies the surface active agent to manifold 16 through electrically controlled valve 30. Flow controller 34 is operatively connected to flow transducer 32 to control the speed of pump 28 and thereby control the concentration of surface active agent within manifold 16.

Cationic surfactants which can be employed include quaternary amino or nitrogen compounds; quaternary ammonium salts such as benzalkonium chloride, alkyltrymethylammonium salts, and alkylpyridinium salts; aliphatic mono-di, and polyamines; rosin-derived amines; amine oxides, such as polyoxyethylene alkyl and alicyclic amines, N, N, N, N tetrakis-substituted ethylene diamines, amide-linked amines, preferably those prepared by the condensation of a carboxylic acid with a di- or polyamine, and sodium tauro-24, 25-dihydrofusidate.

Anionic surfactants which can be employed include sulfates such as alkyl sulfates (for example, sodium dodecyl sulfate), sulfated fats and oils, sulfated oleic acid, sulfated alkanolamides, sulfated esters, and alcohol sulfates; sulfonates such as alkylaryl sulfonates, olefin sulfonates, ethoxylated alcohol sulfates, and sulfonates of ethoxylated alkyl phenols; sulfates of fatty esters; sulfates and sulfonates of alkyl phenols; lignosulfonates; sulfonates of condensed naphthalenes; sulfonates of naphthalene, dialkyl sulfosuccinates, preferably sodium derivatives; sodium derivatives of sulfo-succinates, such as the disodium ethoxylated nonyl phenol half ester of sulfosuccinic acid, the disodium ethoxylated alcohol ($C_{10}$–$C_{11}$), half-ester of sulfosuccinic acids, etc., petroleum sulfonates, such as alkali salts of petroleum sulfonates; for example, sodium petroleum sulfonate (Acto 632); phosphate esters, such as alkali phosphate esters, and a potassium salt of phosphate ester (Triton H66); sulfonated alkyl esters (for example, Triton GR 7); carboxylates, such as those of the formula (RCOO)—(M)+ wherein R is an alkyl group having from 9–21 carbon atoms, and M is a metal or an amine; and sodium polymeric carboxylic acid (Tamol 731) and the like.

Non-ionic surfactants which can be employed include polyoxyethylenes; ethoxylated alkyl phenols, ethoxylated aliphatic alcohols; carboxylic acid esters, such as glycerol esters, polyethylene glycol esters, and polyoxyethylene fatty acid esters; anhydrosorbitol esters and ethoxylated anhydrosorbitol esters; glycol esters of fatty acids; ethoxylated natural fats, oils, and waxes; carboxylic amides, such as diethanolamine condensates, and monoalkanolamine condensates; polyoxyethylene fatty acid amides; polyalkylene oxide block copolymers, preferably polyethylene and polypropylene oxide block copolymers; and polysiloxane-polyoxyalkylene copolymers; 1-dodecylazacyeloheptan-one polyethylene glycol monolaurate; and Macrochem's SEPA non-ionic surfactant.

Preferred non-ionic surfactants are ethylene oxide condensation products (polyoxyethylene) containing more than two, and preferably at least five, ethylene oxide groups with at least one end group thereof being terminated by reaction with either an alcohol, alkylphenol or a long chain fatty acid. A particularly preferred non-ionic surfactant is an octylphenoxy polyethoxyethanol surfactant known as Triton X-100.

Amphoteric surfactants include N-coco-3 aminopropionic acid and its sodium salt; disodium salts of N-tallow-3-iminodipropionate and N-lauryl-3-iminodipropionate; N-carboxymethyl-N cocoalkyl-N-dimethylammonium hydroxide; N-carboxymethyl-N-dimethyl-N-(9 octadecenyl) ammonium hydroxide; (1-carboxy heptadecyl) trimethylammonium hydroxide; (1-carboxyundecyl) trimethylammonium hydroxide; sodium salts of N-cocoamidoethyl-N-hydroxyethylglycine and N-hydroxyethyl-N-stearamido-glycine; sodium of salts of N-hydroxyethyl-N-lauramido-B-alanine and N-cocoamido-N-hydroxyethyl-B-alanine; sodium salts of mixed alicyclic amines, ethoxylated and sulfated sodium salts or free acids of 2-alkly-1-carboxymethyl-1-hydroxyethyl-2-imidazolinium hydroxide; the disodium salt of 1. 1-bis (carboxymethyl)-2-undecyl-2-imidazolinium hydroxide; and the sodium salt of a propoxylated and sulfated oleic acid-ethylenediamine condensate.

Another fluid subsystem, e.g., fluid subsystem 22, can include a source of acid 36 which is supplied to manifold 16 via inlet and outlet valves 38 and 40 by pump 42. A pH controller 44 is operatively associated with pH transducer 46 mounted on manifold 16 to control the speed of acid pump 42 and maintain the treatment solution in manifold 16 at a constant pH. Preferably, pH controller 44 also is operatively associated with flow transducer 32 to maintain a more precise control over acid delivery. Acids which can be employed in this operation include inorganic acids such as hydrochloric acid and organic acids such as peracetic acid. After acid treatment, the bone is rinsed with sterile water for injection, buffered with a buffering agent to a final predetermined pH and then finally rinsed with water for injection to remove residual amounts of acid and buffering agent.

Another fluid subsystem, e.g., fluid subsystem 24, can include a source of ethanol 48 which is supplied to manifold 16 through electrically controlled valves 50 and 52 by pump 54. Controller 56 is operatively connected to pressure transducer 33 mounted on chamber 12 to control the speed of ethanol pump 54. The overall sequence and timing of the operations of subsystems 20, 22 and 24 are controlled by operator input and a master controller 58, which is operatively associated with flow transducer 32, to coordinate operation of each of these subsystems. Each subsystem can be operated alone or in combination with any of the other subsystems to treat bone.

Other fluids can also be provided in system 10 in addition to or in combination with those already mentioned. For example, a preferred defatting/disinfectant solution is an aqueous solution of ethanol and non-ionic surfactant, the ethanol being an effective solvent for lipids and the water being an effective hydrophilic carrier to enable the solution to penetrate more deeply into the bone. The aqueous ethanol solution also disinfects the bone by killing vegetative microorganisms and viruses. For example, the non-ionic surfactant destroys the lipid toga viruses such as HIV and HBV. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is about 60% to 85% alcohol and most preferably about 70% alcohol.

Medically/surgically useful substances which can be supplied by pressure flow system 10, in addition to those set forth above include, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; amino acids, magainins, peptides, vitamins, inorganic elements, co-factors for protein synthesis; hormones; endocrine tissue or tissue fragments; synthesizers, enzymes such as collagenase, peptidases, ozidases, etc.; surface cell antigen eliminators; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents, immunosuppressants; permeation enhancers, e.g., fatty acid esters such as laureate, myristate and stearate monoesters of polyethylene glycol, enamine derivatives, alphaketo aldehydes, etc.; nucleic acids, and, biorodable polymers such as those disclosed in U.S. Pat. Nos. 4,764,364 and 4,765,973 and European Patent Application 168,277. The amounts of such optionally added substances can vary widely with optimum levels being readily determined in a specific case by routine experimentation.

The following is an example of a preferred operating cycle of pressure flow system 10 for treating bone:

After bone section 62 is secured in pressure chamber 12, as illustrated in FIG. 6, water pump 19 and pump 28 are operated to supply a solution of known concentration to pressure chamber 12. The particular solution selected will depend upon the type of treatment process being performed. Fluid can be supplied to more than one chamber 12 simultaneously, i.e., multiple pressure chambers can be provided to concurrently treat a plurality of bones or bone sections. The duration of flow can vary depending upon the type of bone being cleaned. After a specified duration, pump 28 is shut off while water pump 19 is operated to flush the system. After a specified duration of flushing, water pump 19 is shut down and ethanol pump 54 is operated to flush the vasculature and the porous structure of the bone.

In an alternate embodiment of the bone cleaning process, after the bone has been flushed with an initial treatment solution, the medullary canal of bone 62 can be sealed using seal 78 (FIG. 6). Thereafter, fluid passing through the bone is forced to flow through the cancellous tissue of bone and subsequently exit the bone through the cortical tissue of bone rather than through the medullary canal.

Bone is composed of two types of tissue, cortical tissue and cancellous tissue. The periosteal portion of bone is formed of cortical tissue which has a porous structure with a large quantity of solid matter. The endosteal portion of bone is formed of cancerous tissue which has a sponge-like appearance and also includes a porous structure having smaller amounts of solid matter. The relative quantity of each kind of tissue varies in different bones and within different parts of the same bone to meet the requisite strength requirements of the bone. The interior of long bones includes a central cavity called the medullary canal (See, FIG. 7).

During treatment of bone using pressure flow system 10, fluid from within chamber 12 is forced to flow from the periosteal portion of bone 62 to the endosteal portion of bone 62 to a position beyond seal 66 within a portion of bone 62 located outside chamber 12. The fluid is then forced to flow from the endosteal portion of the bone to the periosteal portion of the bone to exit bone 62 outside chamber 12. It has been discovered that forcing the treatment fluid to flow along the natural circulatory path of bone, i.e., from the endosteal portion of bone to the periosteal portion of bone, results in more uniform and deeper fluid penetration into the bone matrix, especially in the cortical tissue of bone.

Figure 8:
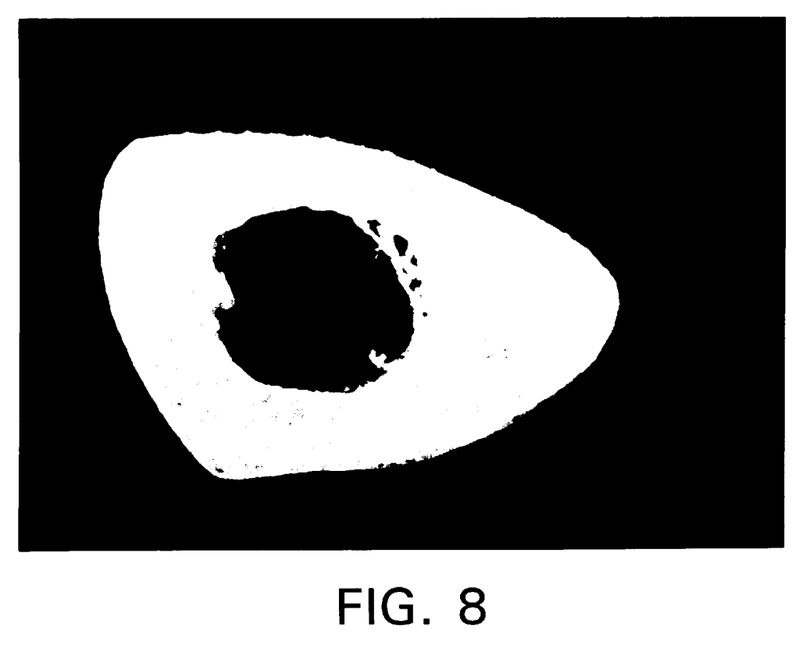
FIG. 8 is a photograph of a cross-section of an untreated portion of bone.

The treatment solution can be caused to flow under a wide range of pressures. The low end of the pressure range is limited only by the resistance of the bone microvasculature. Physiological pulse pressure in bone is approximately 10 mm Hg and a pressure differential of this value or greater would be expected to enact some level of flow in this system. The upper end of the pressure range is expected to be the pressure at which physical or biological damage occurs to the bone. Experiments have been performed up to approximately 50 psi with no deleterious effects noted. Higher pressure would also be expected to be satisfactory. The following examples illustrate bone cleaning operations employing the pressure flow system of this invention, and for purposes of comparison, the vacuum method described in U.S. Pat. Nos. 5,513,662 and 5,556,379, the high pressure spray method described in U.S. Pat. No. 5,333,626, and an untreated portion of bone (FIG. 8).

EXAMPLE 1

Pressure Flow System of this Invention

Figure 9:
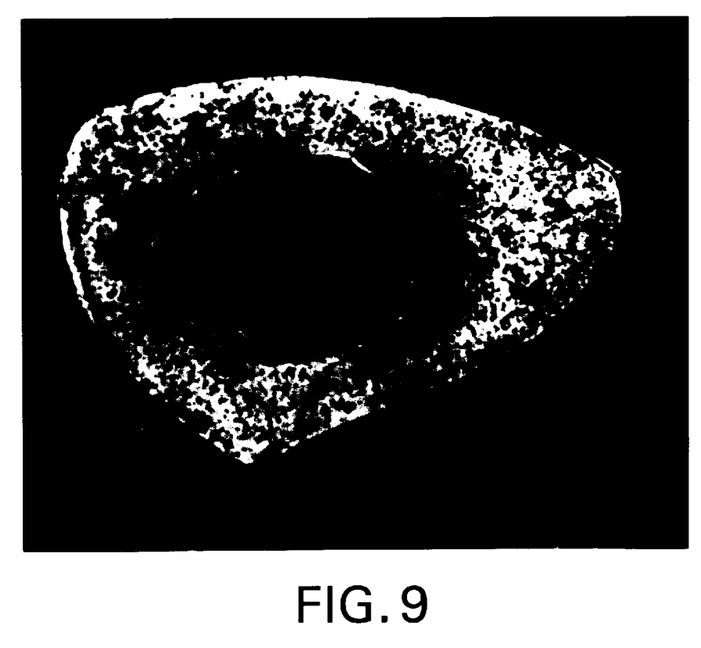
FIG. 9 is a photograph of a cross-section of a portion of bone treated using the pressure flow system of this invention.

A human right proximal tibia was debrided of all soft tissue and periosteum. A cut was made with a hand saw in the mid-shaft area. The proximal portion (approximately 18 cm in length) was fixed into the pressure flow system with an inflatable seal so that the proximal head was inside the chamber and most of the shaft was outside. The chamber was filled with 1% Triton X-100™ (at 40° C.) and pressure established. Fluid was observed to flow out of the open medullary canal. At first, the fluid was red in color and quite turbid. After a total of 3.75 L of solution had flowed through the bone (in approximately 2 minutes), the solution was virtually clear and flow was stopped. These findings were checked by analyzing the effluent with a spectrophotometer to determine absorbance of the solution. The canal was now plugged and flow again established with warm 1% Triton X-100. The solution was now observed to flow in a multitude of small rivulets from the surface of the cortical mid-shaft. After approximately 1 L of solution had flowed through bone (in approximately 3 minutes), flow was stopped and fluid in chamber was changed to 37° C. tap water. Flow was again established until approximately 1.3 L flowed through one in approximately 5 minutes. Fluid in the chamber was now changed to an aqueous solution of methylene blue dye. Flow was established until approximately 1 L of dye had flowed through bone in approximately 4 minutes. Flow was stopped, the bone was removed from the apparatus and a cross-sectional piece was cut approximately 3 cm from the open canal end. See FIG. 9. Outer, inner, and cross-sectional surfaces were observed to be stained blue. A thin slice of the cross-section was ground down further, mounted on a slide and examined microscopically. Every Haversian and Volksmann canal was noted to contain dye and virtually all the osteocytic lacunae were also noted to be blue.

EXAMPLE 2

Vacuum Method of U.S. Pat. No. 5,556,379

Figure 10:
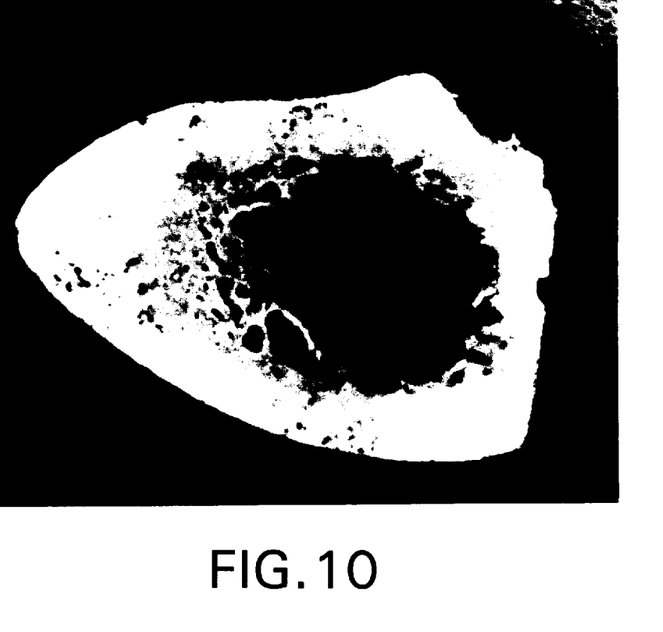
FIG. 10 is a photograph of a cross-section of a portion of bone treated using the vacuum method; and, FIG. 11 is a photograph of a cross-section of a portion of bone treated using the high pressure spray method.

A human left tibia (from the same donor as in example 1) was debrided of all soft tissue and periosteum. A cut was made with a hand saw in the mid-shaft area. The canal of the proximal portion (approximately 18 cm in length) was cleaned of virtually all marrow using a curette and water lavage. A vacuum line was attached to the open end of the bone using an inflatable seal to form an airtight junction. The bone was then submerged in a container of 1% Triton X-100™ (at 45° C.) and vacuum was established using a vacuum pump. Pump was adjusted to provide a steady flow of liquid through the bone and into a trap. Approximately 3.5 L was pulled through in about 11 minutes when vacuum was stopped. Next, bone was placed in a container of warm tap water and vacuum was again established to pull approximately 2 L of water through the bone in about 5 minutes. Next, bone was placed in a container of aqueous methylene blue dye solution and approximately 1.5 L was pulled through in about 4 minutes. Bone was removed from apparatus and a cross-sectional piece was cut approximately 3 cm from the open canal end. See FIG. 10. Outer and inner surfaces were observed to be stained blue but only a thin ring near the outer and inner surface was observed to be blue on the cross-sectional surface. Most of the interior remained yellow to white. A thin slice of the cross-section was ground down further, mounted on a slide, and examined microscopically. Less than 50% of Haversian and Volksmann canals were observed to contain dye and few of the osteocytic lacunae were stained blue.

EXAMPLE 3

High Pressure Spray System of U.S. Pat. No. 5, 333,626

A human right distal tibia (from same donor as Examples 1 and 2) was debrided of all soft tissue and periosteum. A cut was made with a hand saw in the mid-shaft area. The canal of the proximal portion (approximately 18 cm in length) was cleaned of virtually all marrow using a curette and water lavage. A high pressure spraying system and spray gun were operated at approximately 2000 psi to deliver the following solutions:

(A) Ten liters of TRITON X-100 at 45° C.;
(B) Ten liters of water; and
(C) Four liters of methylene blue dye in aqueous solution.

Figure 11:
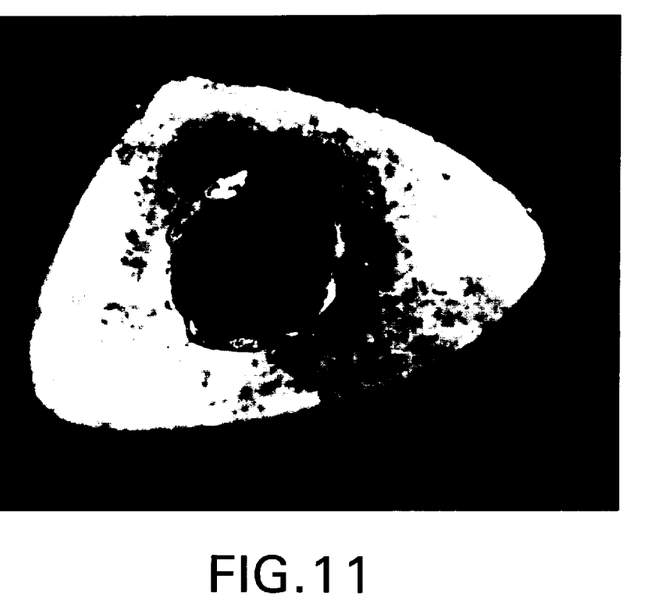

The spray was focused on one spot in the cortical mid-shaft area. Next, a cross-sectional piece was cut through the cortical mid-shaft. (See FIG. 11) Outer and inner surfaces were observed to be stained blue with fair penetration of the inner surfaces directly below the focal point of spray. Evidence of full penetration was absent outside of the focal point of the spray.

It is apparent after viewing FIGS. 8–11 that the osteocytic lacunae, which are the smallest recesses of bone, can be thoroughly accessed via the pressure flow system, while a much smaller percentage can be reached using the vacuum method and the high pressure spray method when the systems are run under comparable parameters and conditions.

As discussed above, pressure flow system 10 can be used to perform treatment procedures besides cleaning. For example, pressure flow system 10 can be used to effect demineralization of bone by forcing an acid or other demineralizing agent through the bone. This can be accomplished by activating water pump 19 and acid pump 42 to supply an acidic solution to pressure chamber 12. After a specified duration, acid pump 42 can be deactivated and water pump 19 operated alone to flush the acid from the bone. Where bone has any significant cross-sectional dimension, current methods of demineralization (e.g., acid bath) result in demineralization progressing by a solvent front process. This results in bone which retains some amount of mineral matter that increases towards its center. By contrast, the pressure flow system described herein provides a demineralized bone possessing a more uniform demineralization profile than such current methods, essentially increasing the porosity by demineralizing the vascular channels throughout the bone.

This system is intended to be used to develop allograft forms that can provide structural support, but that have enhanced ability to be remodeled into host bone due to improved vascular access through the demineralized microporous structure of bone. This process will allow for development of osteoinductive weight bearing allografts.

It will be understood that various modifications can be made to the embodiments disclosed herein. For example, the flow system need not be used for cleaning or demineralization but can instead be used as a histology tool. Because the pressure flow system described above has proved to be effective at penetrating mineralized tissue, the system can be used to inject a dye or any other suitable contrasting agent, e.g., a methylene blue dye, into the smallest recesses of bone including the osteocytic lacunae to improve visualization of these minute structures and to better enable the study of the microvasculature of bone. The chamber can also be used to study fluid flow mechanics through bone microvasculature. It can also be used to impregnate bone with pharmacological agents (antibiotics, bone growth factors, etc.) so the bone can act as a delivery system. Further, more than one pressure chamber can be used concurrently to treat one or several workpieces. For example, a whole bone can be treated by securing one end of the bone within a first pressure chamber and the other end of the bone within a second pressure chamber. In yet another example, a pressure chamber can include more than one opening having a seal positioned in each opening to facilitate simultaneous treatment of several workpieces employing a single chamber. Therefore, the above description should not be construed as limiting, but merely as exemplifications of preferred embodiments. Those skilled in the art will envision other modifications within the scope and spirit of the claims appended thereto.

What is claimed is:

1. A pressure flow system for treating the interior of permeable bone with a fluid which comprises:
    a) a fluid pressure chamber having a fluid inlet port and an opening formed through a wall of the chamber sized to allow passage of at least a portion of the bone therethrough;
    b) a pressurizable seal positioned about the opening conformable to the surface of the bone and capable of fluid-tight engagement therewith; and
    c) a source of pressurized fluid having a pressure greater than atmospheric pressure,
    wherein when the fluid pressure chamber is pressurized to a pressure greater than atmospheric pressure, fluid from the pressure chamber flows from the pressure chamber through the interior of the bone and exits the bone outside the pressure chamber.

2. A pressure flow system as in claim 1, wherein the pressurizable seal is pressurized with a gas or a liquid.

3. A pressure flow system according to claim 1, further comprising a retainer for preventing movement of the bone.

4. A pressure flow system according to claim 3, wherein the retainer includes a plate adjustably affixed to the exterior of the fluid pressure chamber.

5. A pressure flow system according to claim 4, further comprising a sealing device supported by the retainer, the sealing device being positioned to engage and seal one end of the bone.

6. A pressure flow system according to claim 1, further comprising at least first and second fluid sources communicating with the fluid inlet port.

7. A pressure flow system according to claim 6, wherein the first fluid source is a surface active agent and the second fluid source is alcohol.

8. A pressure flow system according to claim 7, wherein the surface active agent is an octylphenoxy polyethoxy ethanol.

9. A pressure flow system according to claim 6, further comprising control means for automatically controlling the ratio of first and second fluids supplied to the pressure chamber by the first and second fluid sources.

10. A method for treating the interior matrix of bone which comprises:
    a) providing a fluid pressure chamber;
    b) positioning at least a first portion of a bone within the interior of the fluid pressure chamber and at least a second portion of the bone outside the fluid pressure chamber; and
    c) supplying a fluid at a pressure greater than atmospheric pressure to the fluid pressure chamber to force the fluid to flow from within the chamber through the interior matrix of the bone to a location outside the fluid pressure chamber.

11. A method according to claim 10, further comprising the step of providing an adjustable seal about an opening in the fluid pressure chamber, the adjustable seal providing a fluid-tight seal about the bone.

12. A method according to claim 10, wherein the fluid is selected from the group consisting of water, soaps, solvents, bioactive agents, sterilization agents, antimicrobials, preservatives, dyes, and demineralization agents.

13. A method according to claim 10, wherein the step of supplying fluid includes supplying at least first and second fluids.

14. A method according to claim 12, wherein the fluid includes a soap and is supplied to clean and/or disinfect the internal matrix of the bone.

15. A method according to claim 14, wherein the soap is a surface active agent selected from the group consisting of cationic surfactants, anionic surfactants, non-ionic surfactants, and amphoteric surfactants.

16. A method according to claim 12, wherein the fluid is a demineralization agent which includes an acid.

17. A method according to claim 12, wherein the fluid is a dye which stains the internal matrix of the bone.

18. A method according to claim 12, wherein the step of supplying a fluid includes sequentially supplying a surface active agent and ethanol.

19. A method according to claim 18, further comprising the step of automatically controlling the sequence and timing of the supply of fluids.

20. A method according to claim 12, wherein the fluid is a bioactive agent selected from the group consisting of bone morphogenic proteins, bone active agents, transforming growth factors, insulin-like growth factors, and other growth factors.

21. A method according to claim 10, wherein the fluid is selected from the group consisting of pharmacologic agents.

22. A method for treating the interior matrix of bone which comprises forcing a treatment fluid at a pressure greater than atmospheric pressure to flow from the endosteal portion of the bone to the periosteal portion of the bone along the natural circulatory path of bone to exit the bone.

23. A method according to claim 22, wherein the treatment fluid is selected from the group consisting of water, soaps, solvents, bioactive agents, sterilization agents, antimicrobial preservatives, dyes, and demineralization agents.

24. A method according to claim 23, wherein the treatment fluid includes a soap and is supplied to clean and/or disinfect the interior matrix of bone.

25. A method according to claim 24, wherein the soap is a surface active agent selected from the group consisting of cationic surfactants, anionic surfactants, non-ionic surfactants, and amphoteric surfactants.

26. A method according to claim 22, wherein the treatment fluid is a demineralization agent.

27. A method according to claim 22, wherein the treatment fluid is a dye.

28. A method according to claim 22, wherein the fluid is a bioactive agent selected from the group consisting of bone morphogenic proteins, bone active agents, transforming growth factors, insulin-like growth factors, and other growth factors.

29. A method according to claim 22, wherein the treatment fluid is selected from the group consisting of pharmacologic agents.

* * * * *